United States Patent
Yang et al.

(10) Patent No.: US 6,861,536 B2
(45) Date of Patent: Mar. 1, 2005

(54) AMINOTHIOL COMPOUND

(75) Inventors: Teng-Kuei Yang, Taichung (TW); Nan-Kuang Chen, Taichung (TW); To Liu, Taichung (TW)

(73) Assignee: National Chung-Hsing University, Taichung (TW)

( * ) Notice: Subject to any disclaimer, the term of this patent is extended or adjusted under 35 U.S.C. 154(b) by 52 days.

(21) Appl. No.: 10/039,557

(22) Filed: Jan. 8, 2002

(65) Prior Publication Data

US 2003/0153781 A1 Aug. 14, 2003

(51) Int. Cl.$^7$ ............................................. C07D 207/04
(52) U.S. Cl. ..................................................... 548/570
(58) Field of Search ................................. 548/570, 571; 564/440, 453; 568/67, 69, 77

(56) References Cited

PUBLICATIONS

Hsu, et al, 2001, J. Org. Chem, 66, 8573–8584.*
Kossenjams, et al, 1999, J. Chem. Soc., Perkin Trans., 1, 2353–2365.*
Kang et al, 1997, CAS:126:131036.*
Kang et al, 1995, CAS:122:55341.*
Carreno et al., 1990, CAS:113:131411.*

* cited by examiner

*Primary Examiner*—Rita Desai
*Assistant Examiner*—Robert Shiao
(74) *Attorney, Agent, or Firm*—Charles E. Baxley

(57) ABSTRACT

The present invention discloses an aminothiol compound having a general formula I wherein $R^1$–$R^5$ are substitutable ligands. Such compounds can perform as superior catalysts in asymmetric addition reactions of organic zinc and aldehyde. According to the present invention, the compounds is needed only less than 0.02% of main reactants to obtain enantioselectivity higher than 99% enantiomeric excess, whereby the asymmetric reactions can become very economic.

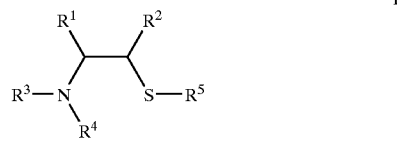

1 Claim, No Drawings

AMINOTHIOL COMPOUND

BACKGROUND OF THE INVENTION

1. Field of the Invention

The present invention relates aminothiol compounds which perform as superior catalysts in the asymmetric addition reactions of organic zinc and aldehyde.

2. Description of the Related Technology

For preparing secondary alcohols, one of the most important methods is to react organic zinc with aldehyde in addition reactions. In order to accelerate this reaction, chiral aminoalcohols are usually added as ligands to combine with organic zinc. Such chiral aminoalcohol create an asymmetric reaction environment, so that one of the produced chiral secondary alcohols is produced more than its stereoisomer, i.e., the asymmetric addition reactions. Apparently, the crux of obtaining a high chemical yield as well as enantioselectivity in the above reactions is to select proper chiral compounds which can provide excellent asymmetric environment for catalytical process.

Though many chiral compounds used in the addition reactions regarding organic zinc and aldehyde can achieve good enantioselectivity, however, these compounds have to be added at an amount at least 1% of the main reactants, and usually around 20%. Additionally, the enantioselectivity always decays with decreasing amount of the chiral ligands used. In general, the enantioselectivity is reduced below 90% enantiomeric excess (e.e.) when the chiral ligands are descended under 5%, so that most of above reactions are not good enough for industrial usage.

Aminoalcohols with optical activity, such as N,N-dibutylnorephe-edine, are frequently applied to accelerating the asymmetric addition reactions of organic zinc and aldehyde as chiral ligand catalysts. By adding aminoalcohols, enantioselectivity of the above reactions can be reached as high as 99% e.e., but an amount 10–20% of chiral aminoalcohols is need. Therefore, it's an important issue how to reduce the necessary amount of the chiral ligands used in the catalysis, so that it can be an economically efficient process

SUMMARY OF THE INVENTION

The object of the present invention is to provide aminothiol compounds with two chiral centers, which can increase enantioselectivity of asymmetric addition of of organic zinc and aldehyde.

In order to achieve the above object, the present invention discloses the aminothiol compounds, which has a general formula I;

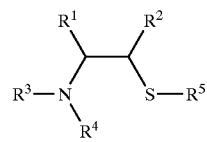

wherein $R^1$–$R^5$ are substitutable ligands.

According to the present invention, the aminothiol compounds can perform as superior catalysts in asymmetric addition reactions wherein organic zinc and aldehyde are involved, In such reactions, though the catalysts are added only 0.1% or even 0.02%, enantioselectivity higher than 99% e.e. can always be obtained. So that such catalyses are economically useful for industries.

DETAILED DESCRIPTION OF THE PREFERRED EMBODIMENTS

In the present invention, aminothiol compounds has a general formula I,

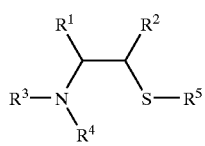

wherein $R^1$ is aryl or alkyl of C1–C9;
$R^2$ is aryl or alkyl of C1–C9;
$R^3$ is alkyl of C1–C9;
$R^4$ is alkyl of C1–C9;
or $R^3$, $R^4$ and N can form a three-to-eight-membered heterocycle; and
$R^5$ can be H or alkyl of C1–C6.

A method for preparing the above ligands and application thereof are as follows:

1. Preparing the ligands

A typical compound of the present invention can be obtained according to the following scheme,

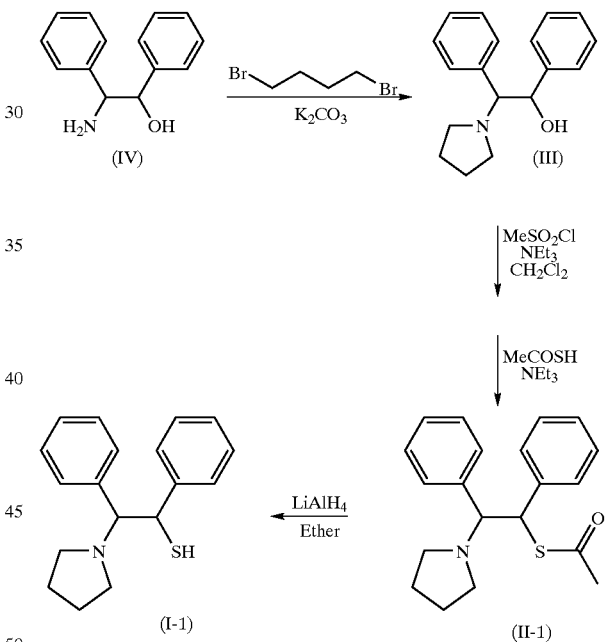

wherein the compound of formula I-1 is obtained by reacting the compound of formula II-1 with LiAlH$_4$ (lithium aluminum hydride).

This method includes steps of:

S11: LiAlH$_4$ and THF (Tetrahydrofuran) are added into a dried three-neck flask under a nitrogen system, the temperature is then regulated to 0° C., and the compound of formula II-1 disolved in THF is added into the flask through an auto-injector in 30 minutes.

S12: Alter the above reactants have completely reacted by stirring for one hour, 15% aqueous NaOH is added to terminate the reaction.

S13: The solution of S12 is filtered through a filter paper, wherein the remained solid is repeatedly washed with a solvent and the filtrate is concentrated by reducing pressure through a vacuum pump to obtain coarse product.

S14: The crude product is then purified through flash column chromatography (Silica gel; eluent is Hex: $Et_3N=$ 100: 1) to obtain white solid.

Further, the compound of formula II-1 is produced by reacting (1R, 2S)-(−)-1,2-diphenyl-2-aminoethanol, i.e., the compound of formula IV, with 1,4-dibromobutane and potassium carbonate to produce the compound of formula III with the cyclic structure as morpholine S21: The compound of formula III is dissolved in dichloromethane under nitrogen, then triethylamine is injected therein, and the temperature is reduced to 0° C.

S22: $MeSO_2Cl$ dissolved in dichloromethane is drop-wisely added into the solution obtained in S21 through a funnel.

S23: After the above solution has completely reacted by stirring for two hours, the aliquote is concentrated by reducing pressure through a vacuum pump, benzene is added therein under nitrogen, and the mixture is heated and refluxed.

S24: Thiolacetic acid and triethylamine are dissolved in benzene and then injected into the mixture of S23.

S25: After the above mixture has completely reacted by stirring for eight hours, $H_2O$ is added therein to terminate the reaction, and the mixture is extracted with dichloromethane for three times.

S26: Anhydrous $Na_2SO_4$ is added into the organic layer obtained in S25 to absorb $H_2O$, which is then filtered and concentrated by reducing pressure through vacuum pump to obtain crude product.

S27: The crude product is purified by column chromatography (Silica get, eluent is n-Hexane: EtOAc: $Et_3N=$100: 1: 1) to obtain a yellow liquid, i.e., the compound of formula II-1.

2. Application of the present invention

The addition reaction of organic zinc and aldehyde can be shown as the following scheme.

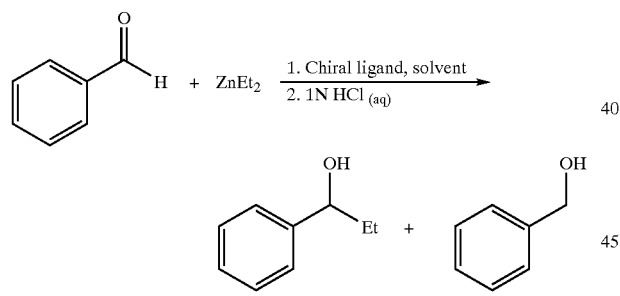

The above scheme includes steps of:

S31: The ligand of formula I-1 (0.03 g, 0.1 mmol) and a dried magnetic stirrer are added into a dried flask.

S32: The flask is sealed and vacuumed to remove moisture and then filled with nitrogen, and then diethylzinc (1.10 mL, 1.2 mmol) is added therein at room temperature and stirred for two hours.

S33: The temperature is adjusted to −20° C., and benzaldehyde (0.11 mL, 1.0 mmol) is added therein and stirred for 12 hours.

S34: 1N aqueous HCl (1 mL) is added into the above solution to terminate the reaction.

S35: The solution of S34 is extracted with acetyl acetate (20 mL), wherein the organic layer is collected and dehydrated with anhydrous $MgSO_4$, and then the mixture is filtered, and the filtrate is concentrated by reducing pressure through an air pump to obtain crude product.

S36: The crude product is purified by column chromatography (Silica gel, eluent is n-Hexane: EtOAc=10: 1).

In order to confirm that high enantioselectivity can be obtained from the present invention, different aminothiol compounds (4d4c, 5d5c) are provided to perform the reactions. The results are listed in Table 1, in which only few values of enantioselectivity are lower than 99% e.e. when the amount of these ligands is 0.02%. Additionally, when the amount of these ligands is 0.1%, all values of enantioselectivity are higher than 99% e.e.

Obviously, the aminothiol compounds in accordance with the present invention are superior than the catalysts exsiting in the literature for the asymmetric addition of organic zinc to aldehyde. In such reactions, though the catalysts are added only 0.1% or even 0.02%, enantioselectivity higher than 99% e.e. are always obtained. Therefore, aminothiol compounds in the present invention are indeed very economic for applying the above asymmetric reactions to industries.

Similarly, the aminothiol compounds in the present invention can be provided as chiral ligands to react with other organic metals, for example, Cu, Ti, etc., to form organometal complexes. These complexes can also react with carbonyl such as aldehyde and ketone, to produce alcohol in the asymmetric addition reactions.

It should be noticed that the above embodiments are only used for explaining the present invention, but not limiting the scope.

TABLE 1

The Ratios of Substrate to Chiral Ligands (S/C)

| Entry[a] | Ligand | S/L | Conversion (%) | 33:34 | e.e. (%) |
|---|---|---|---|---|---|
| 1 | 4d4c | 5000 | 80 | 1:0 | 99.0 (R) |
| 2 | 4d4c | 2000 | 100 | 1:0 | 99.1 (R) |
| 3 | 4d4c | 1000 | 100 | 1:0 | 99.2 (R) |
| 4 | 4d4c | 333 | 100 | 1:0 | 99.3 (R) |
| 5 | 4d4c | 166 | 100 | 1:0 | 99.3 (R) |
| 6 | 4d4c | 100 | 100 | 1:0 | 99.3 (R) |
| 7 | 4d4c | 50 | 100 | 1:0 | 99.4 (R) |
| 8 | 4d4c | 20 | 100 | 1:0 | 99.4 (R) |
| 9 | 4d4c | 10 | 100 | 1:0 | 99.5 (R) |
| 10 | 4d4c | 5 | 100 | 1:0 | 99.5 (R) |
| 21 | 5d5c | 10000 | 68 | 1:0.015 | 98.1 (R) |

TABLE 1-continued

| 22 | 5d5c | 5000 | 81  | 1:0.005 | 98.9 (R) |
| 23 | 5d5c | 2000 | 82  | 1:0.005 | 99.0 (R) |
| 24 | 5d5c | 1000 | 100 | 1:0     | 99.1 (R) |
| 25 | 5d5c | 500  | 100 | 1:0     | 99.1 (R) |
| 26 | 5d5c | 200  | 100 | 1:0     | 99.2 (R) |
| 27 | 5d5c | 100  | 100 | 1:0     | 99.3 (R) |
| 28 | 5d5c | 50   | 100 | 1:0     | 99.3 (R) |
| 29 | 5d5c | 20   | 100 | 1:0     | 99.3 (R) |
| 30 | 5d5c | 10   | 100 | 1:0     | 99.4 (R) |
| 31 | 5d5c | 5    | 100 | 1:0     | 99.4 (R) |
| 32 | 5d5c | 2    | 100 | 1:0     | 99.4 (R) |
| 33 | 5d5c | 1    | 100 | 1:0     | 99.0 (R) |

[a]All of the above reactions used benzaldehyde as the substrate, toluene as the solvent.
[b]3.7 eq. of $Et_2Zn$ was used.
[c]The reaction were carried at −20° C. for 12 hrs.
[d]S/C was the ratio between the substrate and chiral ligand.

What is claimed is:

1. An aminothiol compound, having a general formula I,

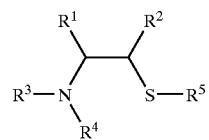

I wherein $R^1$–$R^5$ are substitutable ligands, and
  $R^1$ is aryl;
  $R^2$ is aryl or alkyl of C1–C9;
  $R^3$, $R^4$ and N form a five-membered heterocycle pyrrolidine; and
  $R^5$ is H.

* * * * *